United States Patent [19]

Portman et al.

[11] Patent Number: 5,093,265
[45] Date of Patent: Mar. 3, 1992

[54] METHOD FOR DETECTING OF PREMENSTRUAL SYNDROME

[75] Inventors: Edward M. Portman; Austin L. Shug, both of Madison, Wis.

[73] Assignee: Genesis Systems Corporation, Madison, Wis.

[21] Appl. No.: 133,604

[22] Filed: Dec. 16, 1987

[51] Int. Cl.$^5$ .............................................. G01N 33/50
[52] U.S. Cl. ...................................... 436/65; 436/86; 436/547; 436/811; 514/879
[58] Field of Search ................ 436/501, 504, 518, 65, 436/811, 86, 547; 514/2, 8, 169, 899

[56] References Cited

U.S. PATENT DOCUMENTS 3,284,303 11/1966 Meli .
3,862,311 1/1975 Leeson .
4,012,494 3/1977 Ling .................... 436/518
4,196,188 4/1980 Besins .

OTHER PUBLICATIONS

Chemical Abstracts, Morishige et al., 56585a, vol. 83, p. 329 (Aug. 18, 1975).
Reid and Yen, *Am. J. Obstet. Gynecol.*, V. 1, pp. 88–104 (1981).
Backstrom et al., *Journal of Steroid Biochemistry*, V. 7, pp. 473–476 (1976).
Coulson, *Medical Hypotheses*, 19:243–255 (1986).
Dalton, *J. Steroid Biochem*, V. 20, No. 1, pp. 437–439 (1984).
Rapid LH for Serum, Plasma or Urine, RIA Kit, Double Antibody/PEG, Serono Diagnostics Protocol, pp. 1–22.
Tsong, Chang and Nash, *Journal of Reproductive Immunology*, 7: 139–149, 151–162, and 163–169 (1985).
Tietz, *Clinical Chemistry*, pp. 1031–1032 (1986).
*Gradwohl's Clinical Laboratory Methods and Diagnosis*, pp. 448–450, 5th Ed. (1980).
Jawetz et al., *Review of Medical Microbiology*, p. 344–345, 12th Ed.
Harrison, *Principles of Internal Medicine*, p. 1738 (1987).
Lyon et al., *Journal of Reproductive Medicine*, No. 10, pp. 705–711 (1984).
Maxson et al., *Fertility and Sterility*, V. 44, No. 5, pp. 622–626 (1985).
Dennerstein et al., *British Medical Journal*, 290:1617 (1985).
Gonzalez, *JAMA Medical News*, V. 245, No. 14, 394–1396 (1981).
Healy et al., J. of Clinical Endocrinology and Metabolism, vol. 47(4), pp. 823–828 (1978).
Morishige et al., *Endocrinology*, vol. 96, pp. 1437–1446 (1975).
Pala et al., *Journal of Clinical Endocrinology and Metabolism*, vol. 67(6), pp. 1317–1321 (1988).

Primary Examiner—Sam Rosen
Attorney, Agent, or Firm—Foley & Lardner

[57] ABSTRACT

Premenstrual syndrome (PMS) and other conditions may be diagnosed according to the invention by measuring the level of luteinizing hormone antibodies in the system of a woman subject. A low level of such antibodies as compared to levels measured for non-PMS women indicates that the patient suffers from PMS. A patient identified by this method is then treated as needed, such as by oral administration of progesterone, to alleviate the symptoms of the condition.

7 Claims, 4 Drawing Sheets

FIG. 1

Day of menstrual cycle

FIG. 2

Day of menstrual cycle

FIG. 3

Day of menstrual cycle

FIG. 4

ANTI-LH ANTIBODY AND LH LEVELS IN PMS WOMEN

FIG. 5

ANTI-LH ANTIBODY AND LH LEVELS IN NON-PMS WOMEN

METHOD FOR DETECTING OF PREMENSTRUAL SYNDROME

TECHNICAL FIELD

This invention relates to a method for reliably diagnosing patients suffering from premenstrual syndrome and treating such patients. The invention further provides an immunodiagnostic test for use in such diagnosis.

BACKGROUND OF THE INVENTION

Premenstrual syndrome (PMS) is a widely used name for a condition that occurs in menstruating women. PMS is defined as the occurrence of both physical and emotional symptoms clustered during the second half of the menstrual cycle, which may persist through menstruation with a relatively symptom free period from the end of menstruation to mid-cycle. Approximately 70% of women experience some PMS symptoms, and 20% of this group suffer from some degree of incapacitation.

The symptoms of PMS appear to become more severe with age, particularly after menopause. Premenstrual syndrome is generally considered to be a neuroendocrine dysfunction (hormonal dysfunction.) Psychological symptoms include anxiety, depression, irritability, fatigue, changes in libido, insomnia, angry outbursts, mood swings, and crying for no apparent reason. Neurological symptoms include headaches, dizziness, lack of concentration, altered motor skills, and loss of sense of smell. Other symptoms include acne, herpes, facial pigmentation, breast pain, palpitations, edema, shortness of breath, respiratory problems, abdominal bloating, constipation, food cravings, compulsive eating, and joint and muscle pain. While these symptoms have been identified as the most commonly reported symptoms associated with PMS, other symptoms may occur in individual cases.

Despite the prevalence of PMS, the cause of PMS remains unknown. One current theory proposes that the condition originates in the central nervous system as the result of an imbalance in the production of natural opiates See, e.g., Reid and Yen, *Am. J. Obstet Gynecol.*, v. 139, no. 1, pp. 88-104 (1981). This theory has not been proven in practice. Research has also focused on alterations in the progesterone-estrogen ratio or the level of luteinizing hormone (LH) as the cause of PMS, but no such alterations have been observed. See Backstrom et al., *Journal of Steroid Biochemistry*, vol. 7, pp. 473-476 (1976) and Coulson, *Medical Hypotheses*, 19:243-255 (1986). Low sex hormone binding globulin (SHBG) capacity has also been described as linked to PMS. See Dalton, *J. Steroid Biochem.*, Vol. 20, No. 1, pp. 437-439 (1984).

Prior to the present invention, no conclusive biochemical marker was known for PMS. Diagnosis therefore has depended upon empirical analysis of symptoms. The patient is typically asked to keep a daily chart of symptoms such as the foregoing for a period of at least a month, often longer. The physician is then left with the task of discerning whether a PMS pattern of symptoms is present. This can prove difficult because the symptoms of PMS overlap symptoms of many other conditions, and some patients may suffer from both PMS and another condition which manifests PMS-like symptoms. Thus, this method of detecting PMS is tedious, uncertain, and lacks scientific credibility.

No clear connection has previously been made between human luteinizing hormone (LH) and PMS. LH is a glycoprotein hormone having a molecular weight of about 28,000 secreted by the pituitary in response to gonadotropin releasing hormone produced by the hypothalamus. LH is composed of two dissimilar molecular subunits, referred to as the alpha and beta subunits. It has been proposed that the beta subunit gives the hormone its target organ specificity and immunologic properties. See Rapid LH, Serono Diagnostics Protocol, p.1. HCG, human chorionic gonadotropin, has the same beta subunit as LH, and immunization experiments using hCG have been attempted. See Tsong, Chang and Nash, *Journal of Reproductive Immunology*, 7: 139-149, 151-162, and 163-169 (1985). LH, in combination with follicle stimulating hormone, causes ovarian changes during the female menstrual cycle. An LH surge occurs with ovulation. See generally Johnson et. al., Immunization of Heifers against LH-RH, hCG, and bLH, *J. Amer. Sci.* (in press).

A variety of conventional immunoassay systems are available for detecting the presence of LH in blood, plasma or urine. For such purposes, human LH has been injected into animals, typically rabbits, which generate rabbit-produced anti-luteinizing hormone (anti-LH) antibodies. Such antibodies are then used as part of a conventional immunoassay system, such as a radioimmunoassay. The extent of the reaction between the anti-LH antibodies and the LH present in the patient sample indicates the level of LH in the sample. Such assays are useful for the diagnosis of conditions associated with elevated or decreased levels of LH. See, for example, Tietz, *Clinical Chemistry*, pp. 1031-1032 (1986), Gradwohl's *Clinical Laboratory Methods and Diagnosis*, pp. 448-450, 5th Ed. (1980), Jawetz et. al., *Review of Medical Microbiology*, pp. 344-345, 12th Ed. and the above-noted Serono Diagnostics Protocol at pages 17-18.

One well known assay for LH is a competitive binding radioimmunoassay as described in the above cited Serono Diagnostics Protocol. According to this procedure, LH in a sample competes with $I^{125}$-labelled LH for a limited number of anti-LH antibodies. The amount of radioactive LH bound to anti-LH antibodies is inversely proportional to the amount of LH present in the sample. A second antibody which binds to the anti-LH antibody together with a polyethylene glycol solution are used to precipitate antibody-bound LH and thereby separate it from free (unreacted) LH. After centrifugation and decanting of the supernatant, the precipitate containing the antibody-bound LH, both labelled and unlabelled, may be analyzed in a standard scintillation counter which in effect detects the amount of $I^{125}$ present. This reading is then used to calculate the LH level in the sample by comparison to results obtained for standards containing known amounts of LH. The standard samples are used to create a standard curve (graph) on which the concentration of the test sample may be found by interpolation. The procedure is typically repeated for control samples obtained from a normal subject in order to determine whether the level of LH is depressed, elevated or normal in the patient.

Although anti-LH antibodies have been raised in animals for diagnostic purposes, there has previously been no evidence that such antibodies exist naturally as circulating antibodies in the human body. In general, the immune system of an animal produces antibodies only in response to foreign substances, not to substances which occur naturally in the body. An autoimmune response, i.e. where the body produces an antibody against a substance the body itself produces, is highly unusual. One such autoimmune response has been observed for certain thyroid hormones $T_2$ and $T_3$, as described in Harrison, *Principles of Internal Medicine,* p. 1738 (1987). Harrison further describes detection of such antibodies using labeled hormone.

A variety of methods for treating PMS have been proposed, including diet, exercise, and drug treatments, as described in Lyon et. al., *Journal of Reproductive Medicine,* Vol. 29, No. 10, pp. 705-711 (1984). One such method involves administering the hormone progesterone to a PMS patient. Progesterone is a naturally occurring steroidal sex hormone also known as pregn-4-ene-3,20-dione. Oral administration of progesterone for PMS treatment has been specifically studied. See, e.g., Maxson et. al., *Fertility and Sterility,* Vol 44, No. 5, pp. 622-626 (1985), Dennerstein et. al., *British Medical Journal,* 290:1617 (1985), Dalton, *J Steroid Biochem,* Vol. 20, No. 1, pp. 437-439 (1984) and Gonzalez, *JAMA Medical News,* Vol. 245, No. 14, pp. 1394-1396 (1981).

A wide variety of pharmaceutical compositions containing progesterone and a carrier or vehicle are known. For PMS treatment, oral forms of progesterone, such as those decribed in Meli U.S. Pat. No. 3,284,303 issued Nov. 8, 1966, Leeson U.S. Pat. No. 3,862,311 issued Jan. 21, 1975, and Besins U.S. Pat. No. 4,196,188 issued Apr. 1, 1980, have been found particlarly effective. It has been found, in particular, that oral administration of micronized progesterone in safflower oil as a carrier is effective for treating the symptoms of PMS.

The present invention provides a method for the detection of premenstrual syndrome (PMS) which utilizes a reliable biochemical marker for PMS and thus eliminates the guesswork involved in PMS diagnosis. Patients screened according to this method can then be effectively treated for PMS symptoms as described hereafter.

SUMMARY OF THE INVENTION

The present invention provides a method for detecting certain conditions the most well known of which is premenstrual syndrome (PMS). This method is based on the discovery that natural anti-LH antibodies exist in the human body which circulate in the blood and bind with human luteinizing hormone (LH). Women suffering from PMS have unusually low levels of such antibodies during the menstrual cycle. A method for detecting PMS according to the invention thus involves determining a potential PMS patient's anti-LH antibody level.

According to a further aspect of the invention, a method for detection and treatment of PMS is provided wherein patients diagnosed as suffering from PMS according to the foregoing test for anti-LH antibodies are treated with an agent that favorably affects the relative amounts of LH and anti-LH to relieve PMS symptoms. In one version of this method, such treatment is effected by administration of progesterone which decreases the level of LH in the PMS patient. In a further embodiment of this method, such treatment involves immunizing the patient with the beta subunit of LH in order to stimulate production of anti-LH antibodies.

According to an additional aspect of the invention, an immunoassay for the detection of human anti-LH antibodies is provided wherein labelled LH is reacted directly with a patient sample containing an unknown amount of anti-LH antibodies.

BRIEF DESCRIPTION OF THE DRAWING

The invention will hereafter be described with reference to the accompanying drawing, in which.

DETAILED DESCRIPTION

In the following detailed description of the method of the invention, conditions such as temperature, pressure and the like are generally not critical unless noted otherwise. Unless specified, process steps are carried out at room temperature and atmospheric pressure.

The method of the invention is based in part on the discovery that a substance that undergoes a binding reaction with LH is present naturally in tne human body, particularly in the body of a menstruating woman. The chemical identity of this substance is unknown, but it undergoes a binding reaction with LH in the same manner as LH antibodies raised in animals Thus, this unknown LH binding substance will be referred to hereafter as a human anti-LH antibody, in the sense that it undergoes an immune binding reaction with LH.

LH is a potentially morbid hormone, i.e. it can have toxic effects at sufficiently high levels. Binding of LH with anti-LH antibody most likely negates such toxicity; in effect, the body produces an antibody to control a necessary but potentially harmful hormone A deficiency of anti-LH antibody might accordingly lead to an excess of LH, the toxicity of which may be a major cause of PMS. However, in the prior art no substantial difference in LH levels has been observed for LH in PMS and non-PMS women. Thus, while the data presented below shows an unmistakable correlation between PMS and low levels of anti-LH antibody, the precise cause of PMS remains unclear. The present invention should, however, make it possible to conclusively determine the cause of PMS because a causal link to PMS, the low level of anti-LH antibody in PMS women, has been identified.

This anti-LH antibody circulates in the blood and in other bodily fluids. The amount of this antibody varies widely during the menstrual cycle, but it has been found that women confirmed as suffering from PMS have substantially lower levels of this antibody than non-PMS women throughout the entire menstrual cycle. Thus, a method for detection of premenstrual syndrome, according to the invention involves measuring the level of anti-LH antibodies in a sample obtained from a human female subject. This sample contains an amount of LH antibodies which corresponds to the level of the antibodies in the subject, a deficiency of the antibodies being indicative of PMS. The sample is preferably blood serum or blood plasma.

The measuring step of the foregoing method is preferably an immunoassay for the antibodies. Such an assay involves reacting the patient sample with a reagent containing LH labeled with a marker substance to form complexes of antibodies in the sample with labeled LH, and determining the extent of formation of such complexes by quantitatively detecting the marker substance. In a preferred embodiment set forth in the example below, the marker substance is a radioactive isotope, e.g. $I^{125}$, such that the measured level of radioactivity indicates the extent of the antigen-antibody reaction. Other similar well known immunoassay techniques, such as immunofluoresence, may also be used.

Upon making the measurement of anti-LH-antibodies, the PMS diagnosis may be readily made by comparing the level of the anti-LH antibodies for the patient with a control level to detect a deficiency of the antibodies indicative of PMS. The control level is established previously by, for example, running the test repeatedly on medically comparable normal subjects known not to suffer from PMS.

A preferred embodiment of the invention utilizes an immunoassay system to detect the anti-LH antibodies. The reaction may be described as:

| Ag* | + | Ab | ⇌ | Ab—Ag* | + | Ag* |
| Labelled LH | | Antibody in sample | | Antibody bound LH | | Free (unreacted) Labelled LH |

An excess of labelled LH is present, and the formation of the antibody-labelled LH complexes is directly proportional to the level of anti-LH antibody in the sample. Upon completion of the foregoing reaction, the next step is to separate the complexes (Ab-Ag*) from the unreacted labelled LH and determine by any suitable means the level of the labelling substance. The labelling substance is typically a radioisotope or a substance capable of emitting light. Conventional immunodiagnostic apparatus is used to detect the light, radioactivity, etc. from the labelling substance. These readings are correlated with known standards to determine the relative amount of anti-LH antibody present in the sample. The test is also carried out using control samples from normal subjects to determine whether a deficiency of anti-LH antibodies exists in the system of the patient. If such a deficiency exists, the patient is diagnosed as having PMS.

One such method generally includes steps of obtaining a suitable sample, e.g. blood serum or plasma, from a female subject to be tested, preparing a nonspecific binding sample consisting essentially of an inert diluent, adding to the subject sample and to the nonspecific binding sample a predetermined excess amount of the labelled LH, preparing a total radioactivity sample consisting essentially of the predetermined amount of the labelled LH, agitating each of the samples to mix each sample, incubating each of the subject samples for a period sufficient to allow the reaction which forms the complexes to run substantially to completion, purifying the subject samples and the nonspecific binding samples to obtain solids, preparing test samples using predetermined amounts of the solids and of the total radioactivity sample, and measuring levels of radioactivity for a predetermined time period for each of the test samples to determine levels of radioactivity present in the test samples corresponding to the subject sample, the nonspecific binding sample, and the total radioactivity sample, respectively. A percent binding amount B% may then be calculated using the equation:

$$B\% = \frac{S - NSB}{TR} \times 100$$

wherein S is the level of radioactivity measured for the test sample prepared from the subject sample, NSB is the level of radioactivity measured for the test sample prepared from the nonspecific binding sample, TR is the level of radioactivity measured for the test sample prepared from the total radioactivity sample, and the value of 8% quantitatively indicates presence and severity of PMS in the subject.

The steps of a specific embodiment of this method utilizing a radioimmunoassay system are generally as follows. First, LH labelled with $I^{125}$ is added both to a blood serum sample from the patient and to several standard LH antibody preparations of known concentrations used to make up the standard curve from which the concentration of the sample will be interpolated. All samples are incubated for a period sufficent to allow the binding reaction to go to completion, preferably at least about 24 hours. A second antibody is then added to precipitate the complexes of labelled LH and anti-LH antibodies (LH-AB complexes.) The second antibody is raised by injecting an immunoglobulin fraction (IGF) into an animal different from the animal used to generate the anti-LH antibodies In the example below, the anti-LH antibodies are generated in advance by injecting a rabbit with human LH and harvesting the antibodies from the rabbit. The second antibody is prepared by a similar procedure wherein the rabbit IGF is injected into sheep, whereby the immune system of the sheep generates antibodies of its own against the rabbit antibodies, namely SARGG (sheep anti-rabbit gamma globulin.)

The second antibody enlarges the complex and renders it less soluble, causing it to precipitate. If the patient sample contains no antibody and hence no complexes form, the second antibody will precipitate by itself with only a background amount of radioactivity from trace contamination with $I^{125}$. The sample is again incubated for a period sufficient to allow the antigen-antibody reaction to go to completion, usually at least about 24 hours at room temperature. A polar organic liquid such as polyethylene glycol is added to the sample, which is primarily aqueous, to decrease the solubility of the complexes and accelerate precipitation. The sample is then centrifuged under conditions effective to complete the precipitation. The supernatant is decanted and the remaining solids are allowed to dry.

The solids are then resuspended in water, and a portion of the resulting suspension is placed in a scintillation vial. An effective amount of a scintillation cocktail, e.g. a mixture of organic solvents such as toluene, is added to the vial, and the resulting mixture is placed in a standard scintillation counter for a fixed length of time. The counter registers a number of light emissions indicative of the amount of $I^{125}$ present. The resulting total emissions measured, computed in counts per minute, is used to calculate percent binding using the following equation:

$$\text{Percent binding} = \frac{\text{Sample* (cpm)} - \text{Nonspecific binding sample (cpm)}}{\text{total counts sample (cpm)}} \times 100$$

*Patient sample, standard sample, or control

In the preceding equation, the non-specific binding sample (NSB) is essentially a sample containing an unreactive diluent and $I^{125}$ labelled LH, so that the level of radiation due to nonspecific binding can be taken into account in calculating percent binding for the patient sample. The total counts sample (TC) contains the labelled LH only. The total counts measurement indicates the total cpm when all of the radioactive isotope is carried through to the final measurement. Thus, the percent binding figure represents the percentage of counts attributable to anti-LH antibodies in the patient sample relative to the total possible number of counts for all of the starting labelled LH.

A well known method may be used to convert the percent binding figure into the actual concentration of anti-LH antibodies present in the patient (unknown) sample. Percent binding values for standards of known concentration are used to construct a standard curve using the foregoing equation to plot values of percent binding versus anti-LH antibody concentration in mI-U/ml. Such a curve is then used to determine the concentration of anti-LH antibody in the unknown sample by interpolation using the percent binding measured for the unknown sample. The use of this procedure for determining anti-LH antibody concentration is optional, since it has been found that the percent binding values sufficiently indicate whether or not the patient has a low level of the antibodies.

A clear correlation has been found between the measured percent binding values for possible PMS patients and the actual presence of PMS, as indicated by responsiveness to PMS therapy and the occurrence and severity of PMS symptoms. The following table sets forth this relationship:

TABLE 1

| Percent Binding | PMS Diagnosis |
| --- | --- |
| 0-1.5% | Severe |
| 1.5%-2.5% | Moderate |
| 2.5%-3.5% | Moderate to mild |
| 3.5%-5.0% | Mild |
| 5.0%+ | None |

According to a preferred aspect of the invention, patients tested as having a percent binding value of about 3.5% or less are treated for PMS with effective drug therapy, especially by oral administration of progesterone, as set forth in detail below. For patients in the 3.5-5.0% range, non-drug therapy such as diet, exercise and the like as set forth above may be prescribed, depending upon the circumstances of the individual case.

Figure 1:
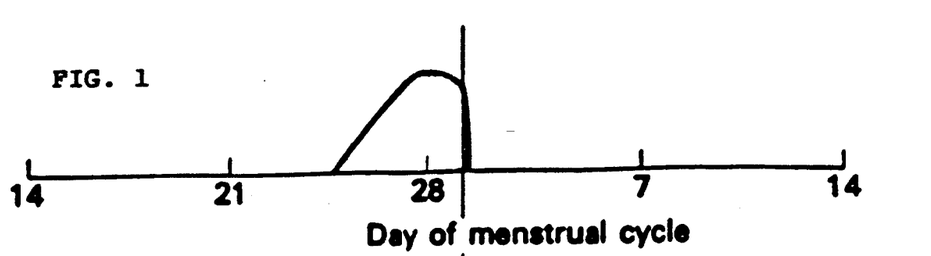
FIGS. 1 through 3 are graphs depicting occurrence and severity of symptoms in PMS women during the menstrual cycle.
Figure 2:
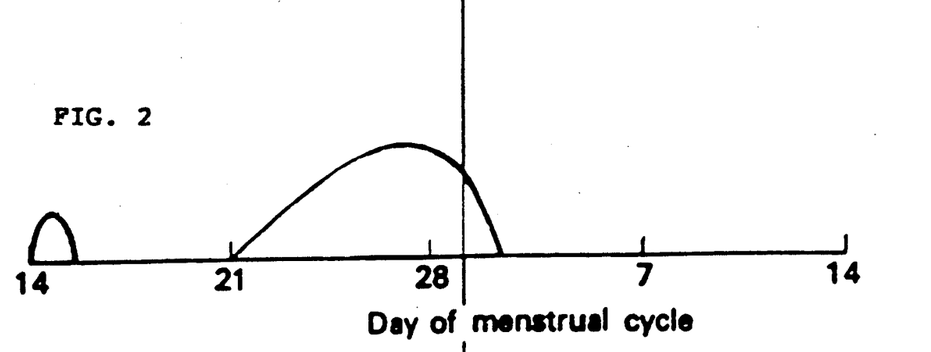
Figure 3:
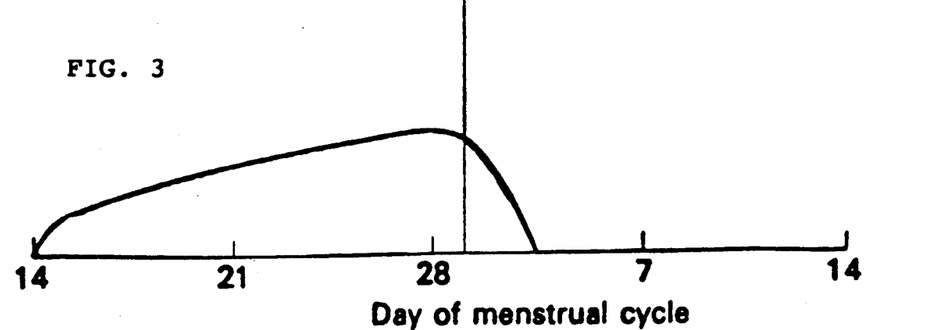

FIGS. 1 through 3 illustrate patterns of PMS symptoms associated with mild, moderate and severe PMS as set forth in Table 1 above. In these graphs, the x-axis represents menstrual cycle time in days and the y-axis represents the relative intensity of the symptoms, as indicated subjectively by PMS patients. FIG. 1 depicts relatively mild PMS during which the patient suffers no symptoms until just before the onset of menstruation. A short burst of symptoms then follows FIG. 2 illustrates a typical pattern for moderate PMS, in which symptoms appear briefly at the time of ovulation (day 14), then disappear for about a week, and then return about a week prior to menstruation (day 29). FIG. 3 illustrates severe PMS, in which symptoms persist from the time of ovulation to after menstruation.

The foregoing method was tested on a group of 39 PMS patients (who met the historical and physical criteria for PMS) and 21 asymptomatic volunteers as a control group. The PMS group did not include any menopausal PMS women. The average percent binding for the PMS patients, based on readings taken at varying times throughout the menstrual cycle, together with the maximum and minimum values (range) for each group were as follows:

TABLE 2

| Group | % Binding | Range | No. of Subjects |
| --- | --- | --- | --- |
| Normal | 5.34 ± 0.31 | 5.96-4.72 | 21 |
| PMS | 2.51 ± 0.21 | 2.93-2.09 | 39 |

The difference between the PMS group and the control group was highly statisically significant ($p$ = less than 0.001) according to the method of Snedecor et. al., Sampling From a Normally Distributed Population, Statistical Methods, Iowa State Univ. Press, pp. 1-593 (1967). The indicated uncertainties are calculated as the standard error of the mean (SEM).

In additional tests, results were obtained by isotope dilution binding tests to determine the specificity of LH binding by anti-LH antibody (Serono preparation) and patient serum anti-LH antibody. Cold (unlabeled) LH specifically diluted out LH-$I^{125}$ in known anti-LH antibody from the Serono Rapid Kit (described below) in the same manner as in a series of five patient serum samples. This indicates specific binding of LH in the serum samples. Since the only known LH binding protein in the serum of mammals is anti-LH antibody, the foregoing results confirmed that LH binding in patient samples is specific binding by anti-LH antibody present in human serum samples.

Figure 4:
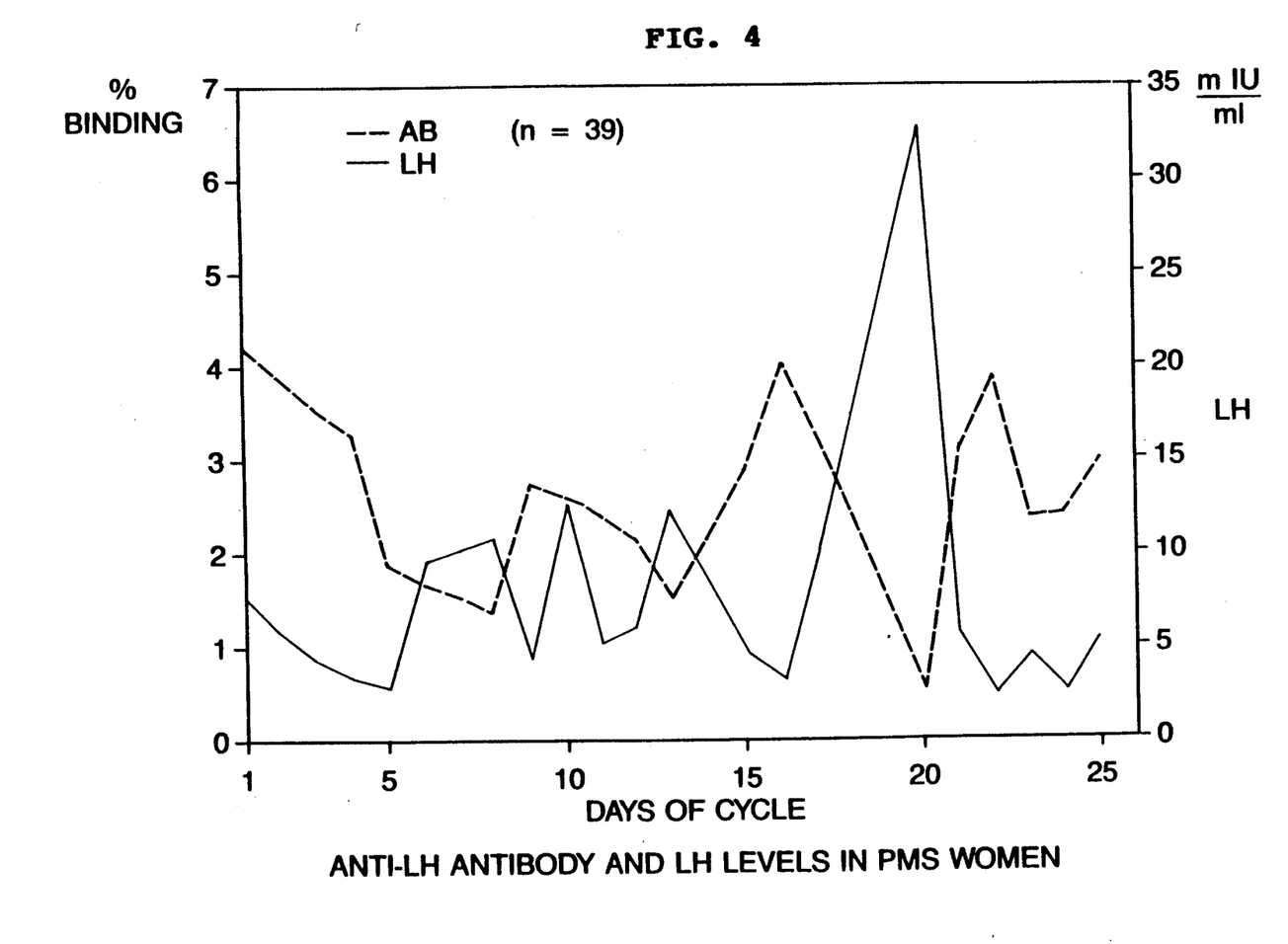
FIG. 4 is a graph, to scale, plotting levels of LH and anti-LH antibody in a test group of women suffering from PMS.
Figure 5:
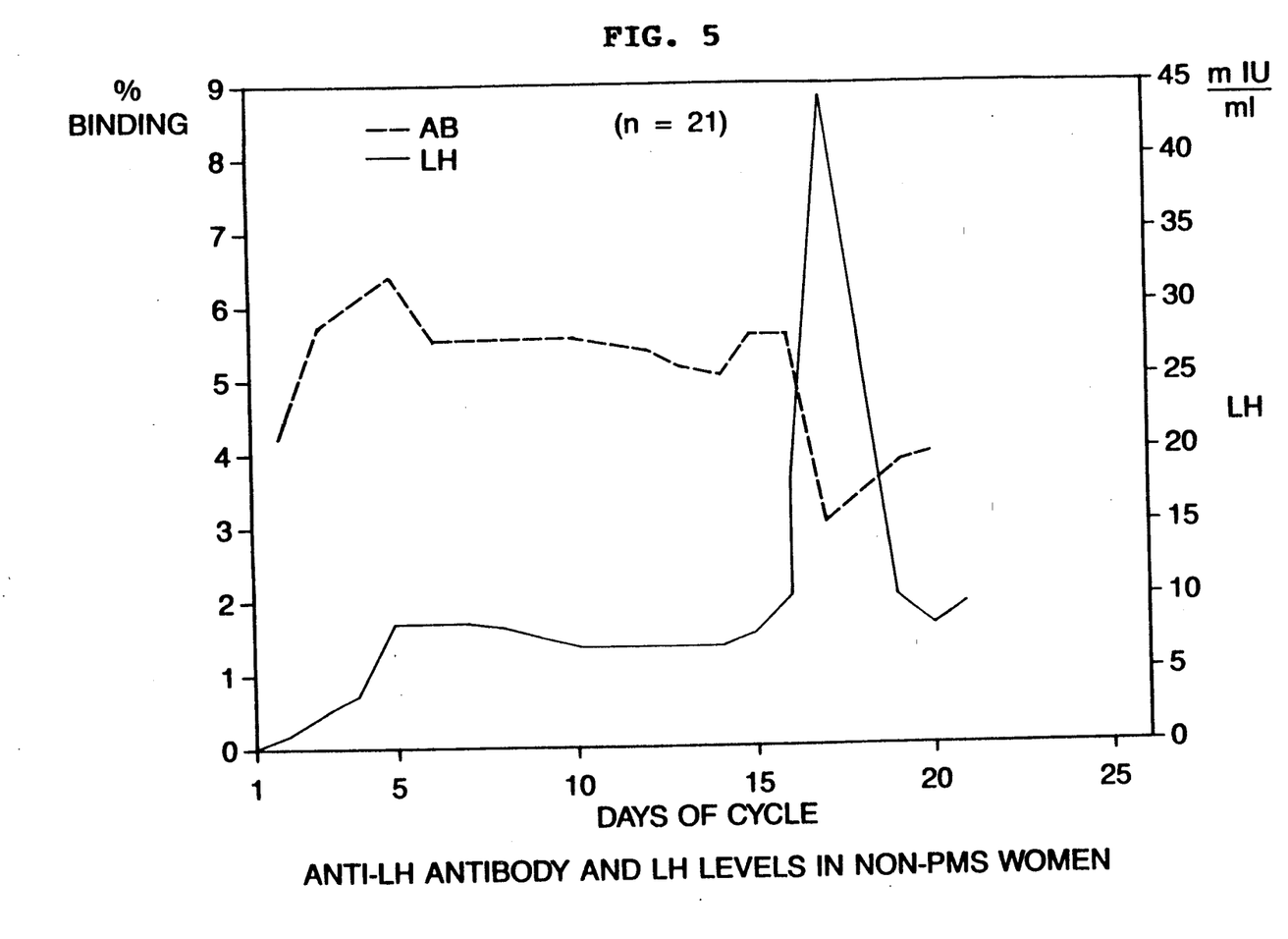
FIG. 5 is a graph, to scale, plotting levels of LH and anti-LH antibody in a test group of non-PMS women.
Figure 6:
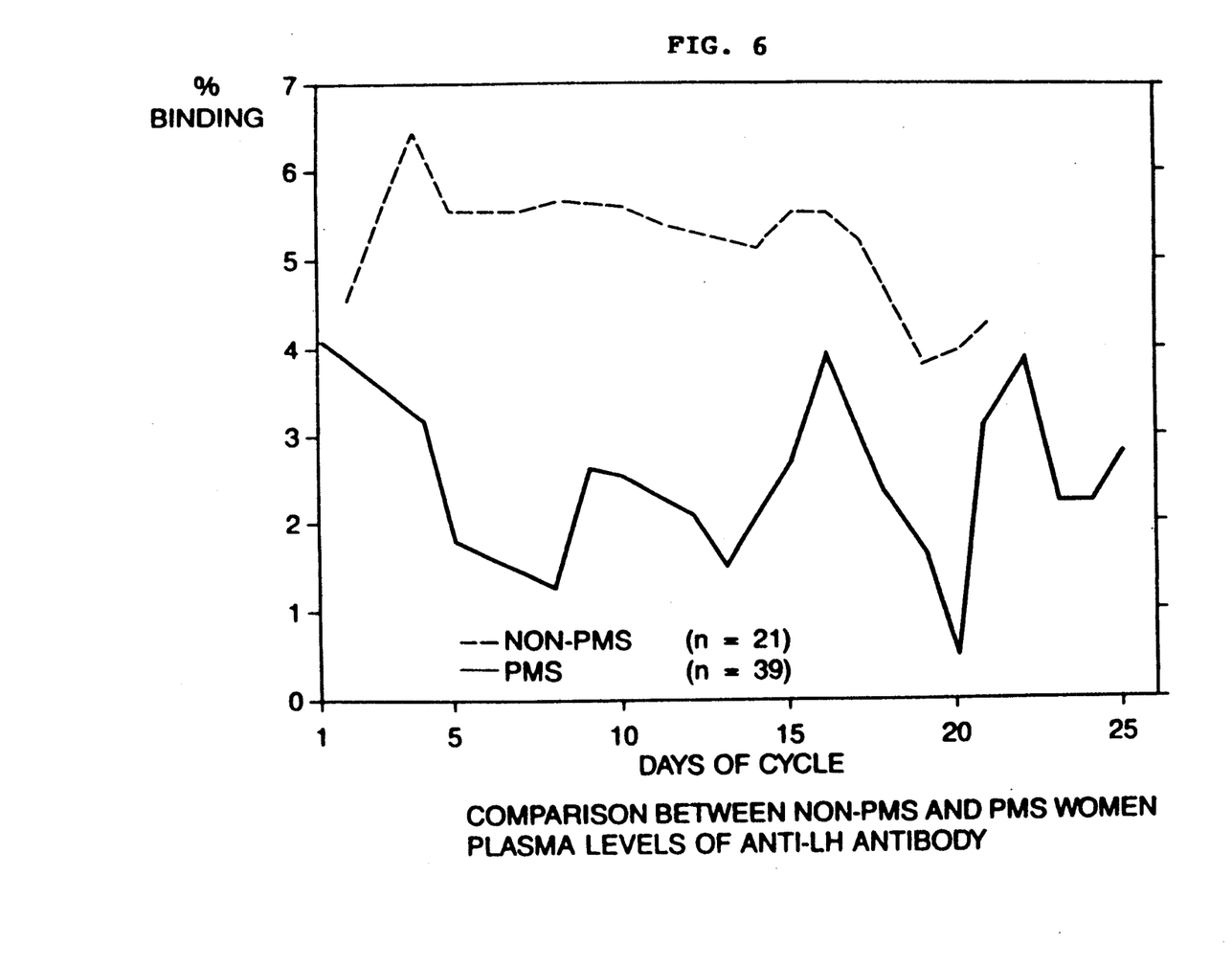
FIG. 6 is a graph, to scale, plotting levels of anti-LH antibody in women suffering from PMS and in non-PMS women, as set forth in FIGS. 4 and 5, on the same scale.

FIG. 4 shows the relative levels of anti-LH antibodies (in % binding, left scale, broken line) and LH (in mI-U/ml, right scale, solid line) in the foregoing PMS patient group. FIG. 5 provides the same showing for non-PMS women of the control group. A comparison of the two graphs indicates that non-PMS women show higher anti-LH antibody levels with relatively little change throughout the cycle, whereas PMS women have generally lower values subject to wider, more sudden variation during the cycle. For this reason, according to an alternative method of the invention, several measurements of anti-LH antibody level are taken at different times throughout the cycle to provide an average value to more accurately assess the severity of the condition. If the patient's cycle is known with. certainty, the diagnosis can take such variations of anti-LH antibody into account. FIG. 6 plots % binding levels for anti-LH antibodies for PMS and non-PMS women, as shown in FIGS. 4 and 5, on the same scale. FIG. 6 shows that the level of such antibodies in PMS women is lower throughout the menstrual cycle than for normal women, notwithstanding the cyclic variations.

As FIGS. 4-6 illustrate graphically, anti-LH levels tend to correspond to (be more representative of) the average anti-LH level for both PMS and non-PMS women during days 5 to 15 of the menstrual cycle.

Clinical studies utilizing the method of the invention have shown an excellent correlation between the various physical and emotional symptoms of PMS patients and their low levels of circulating anti-LH antibodies. Menopausal PMS women are known to suffer from particularly severe symptoms. This was reflected by the results for such women, who consistently tested at 0.0% binding, indicating essentially no circulating free anti-LH antibody present.

Once a positive PMS diagnosis has been made according to the method of the invention, the PMS symptoms may be reliably treated using known techniques, for example, progesterone therapy. The method of treating PMS according to the present invention generally involves administering an agent effective for suppressing LH production, preferably progesterone, to a woman having a low level of anti-LH antibody to reduce the imbalance between LH and anti-LH antibody levels. Such treatment of PMS according to the present invention preferably involves oral administration of a therapeutically effective amount of progesterone to such patient throughout the menstrual cycle. Oral administration is preferred in view of the known disadvantages of other dosage forms for progesterone, such as vaginal suppositories, rectal suspensions, and injections.

A typical treatment, for example, would involve administration of 400 mg daily, in the form of one capsule containing 100 milligrams micronized progesterone in an oil carrier four times per day, usually for a period of about 12-16 consecutive days following the day of ovulation. The daily dosage can vary between 200 and 1200 mg of progesterone per day, 200 to 400 mg per day being more common. A preferred capsule type comprises progesterone micronized to particle sizes of less than about 10 microns dispersed in an effective amount of an unsaturated vegetable oil, especially safflower oil or its equivalent, e.g. an oil for which glycerides of linoleic acid are a major component.

A well-known calendar method can be used to determine the date of ovulation when necessary, and other tests for determining ovulation, for example by body temperature, are available. After the end of each cycle, no further progesterone is taken until the beginning of the next cycle.

Progesterone administration mitigates the symptoms of PMS but does not provide a cure for the condition. According to a further aspect of the invention, a full or partial cure of PMS may be effected by immunizing a PMS woman with the beta subunit of LH. According to this aspect of the invention, a preparation containing the $\beta$-subunit of LH is administered in a conventional manner into the system of the PMS women. The presence of this subunit will stimulate anti-LH antibody production by the woman's own body without having the toxic effects of LH itself. Elevation of anti-LH antibody production by the body should eliminate the need for treatment by regular administration of progesterone or other drugs.

The method of the invention can also be used to detect or determine the severity of other conditions which are associated with low anti-LH antibody levels. Such conditions include susceptibility to carcinomas, including breast carcinoma, uterine carcinoma, and prostatic carcinoma. The method of the invention can also determine the severity of climacteric-menopausal syndrome. In general, the method of the invention can be used in the diagnosis of any medical condition associated with depressed levels of anti-LH antibody.

The following example illustrates a preferred embodiment of the invention wherein PMS is detected by radioimmunoassay and treated by administration of progesterone.

EXAMPLE

A blood sample (5 ml) was obtained from a PMS patient and allowed to clot. The clotted blood was centrifuged to obtain the serum fraction. 200 $\mu$l of the serum was placed in a test tube, in duplicate. 200 $\mu$l of three different standards were similarly placed in test tubes. The standards contained anti-LH antibodies (rabbit gamma globulin), bovine serum albumin (BSA), an inert dye, and 0.1% sodium azide in a tris buffer. Two of the three standards were diluted with LH/FSH diluent (described below) to concentrations of 1/10 and 1/100. The standards were prepared from the LH antiserum preparation included in the Serono Rapid LH Kit, from Serono Diagnostics, Inc.

Nonspecific binding tubes were prepared by placing 200 $\mu$l of LH/FSH diluent (Serono Rapid LH Kit) into a test tube in duplicate. The diluent contains a phosphate buffer, EDTA, BSA, and 0.1% sodium azide.

100 $\mu$l of a reagent containing human LH labelled with $I^{125}$ (Serono Rapid LH Kit) was then added to each of the sample and standard tubes. This reagent contained the labelled LH together with a phosphate buffer, EDTA, BSA and 0.1% sodium azide. An additional 100 $\mu$l of this reagent was placed in a test tube in duplicate to provide total count tubes. All tubes were then vortexed (mixed) at half speed for 5 seconds in a Scientific Products vortexing machine (American Scientific Products Vortex Mixer, No. S8223-1) and allowed to incubate at 24 hours at room temperature.

200 $\mu$l of a second antibody reagent (Serono Rapid LH Kit) containing SARGG, bovine serum, BSA, bovine gamma globulin, an inert dye and 0.1% sodium azide was added to all tubes (samples and standards) except for the total count tubes. The resulting mixtures were vortexed as described above and allowed to stand (incubate) for 24 hours at room temperature.

1.0 ml of a polyethylene glycol solution (Serono Rapid LH Kit) chilled to about 5° C. containing polyethylene glycol (MW 6,000), tris buffer and 0.1% sodium azide was then added to all tubes, except for the total count tubes. All tubes except for the total count tubes were vortexed as described above, then centrifuged at 3200 rpm for 30 minutes at 25° C. (IEC Centra-7R Centrifuge). The supernatant was decanted, and the solid precipitate therein was blotted dry and pelleted. All tubes (including total count tubes) were diluted with 0.6 ml water and allowed to stand for 30 minutes. The pellets were then resuspended by vortexing as noted above.

Test samples (0.5 ml) were removed from each tube and placed in a standard scintillation vial. 4 ml of a conventional scintillation cocktail (Optifluor, Packard Instruments) was added to each tube. Each tube was then loaded into a scintillation counter (Packard Liquid Scintillation Analyzer, Tri-Carb 1500) a 2 minute period were measured. Percent binding for the samples is then calculated according to the equation set forth above using the total counts measured for each of the tubes measured, specifically the sample tubes, nonspecific binding tubes and total count tubes. Optionally, the concentration of anti-LH antibody in the sample may be calculated by preparing a standard curve using the count values obtained for the standard samples of 1, 1/10 and 1/100 dilution.

The percent binding value for the patient sample is compared to known standards (Table 1 above) to determine whether the patient has a low level of anti-LH antibody indicative of PMS. Treatment using an oral progesterone formulation is indicated if the percent binding is about 3.5% or less. The patient then begins taking 4 capsules containing 100 mg micronized progesterone in safflower oil daily during each day of the menstrual cycle. This treatment is continued for as long as needed.

It will be understood that the above description is of preferred exemplary embodiments of the present invention, and the invention is not limited to the specific methods shown. Modifications may be made in the method according to the invention without departing from the scope of the invention as expressed in the appended claims.

We claim:

1. A method for detecting premenstrual syndrome which comprises:
    obtaining a blood sample from a pre-menopausal woman manifesting symptoms of premenstrual syndrome who undergoes menstrual cycle and whose body produces levels of human LH which vary during the course of each menstrual cycle, which blood sample contains an unknown, naturally occurring amount of an anti-LH substance which undergoes a specific binding reaction with human LH, the sample being taken at a time approximately during days 5 through 15 of the menstrual cycle; and
    assaying said sample to determine the amount of human anti-LH binding substance therein, and
    wherein a deficiency of said anti-LH binding substance is indicative of premenstrual syndrome.

2. The method of claim 1, wherein the assaying step further comprises:
    mixing the blood sample with a reagent containing an excess amount of a human LH binding reagent;
    complexing said anti-LH binding substance and said LH binding reagent; and
    detecting the amount of complex formed to determine the level of human anti-LH binding substance in said blood sample.

3. The method of claim 1, further comprising comparing the level of the anti-LH binding substance with a standard level to detect a deficiency of the anti-LH binding substance indicative of premenstrual syndrome.

4. The method of claim 2, wherein said binding reagent comprises human LH labelled with a marker substance.

5. The method of claim 4, wherein said marker substance is a radioactive isotope.

6. The method of claim 4, wherein said detecting step further comprises separating said complex from unreacted labelled LH, and detecting the level of the marker substance in said complex to determine the extent of formation of said complex.

7. The method of claim 6, wherein said marker substance is a radioactive isotope.

* * * * *